United States Patent [19]

Ellis et al.

[11] Patent Number: 4,622,293

[45] Date of Patent: Nov. 11, 1986

[54] IODOTHYRONINE IMMUNOASSAYS EMPLOYING HMS AS TBP BLOCKING AGENT

[75] Inventors: Paul B. Ellis; David L. Morris, both of Elkhart, Ind.

[73] Assignee: Miles Laboratories, Inc., Elkhart, Ind.

[21] Appl. No.: 510,814

[22] Filed: Jul. 5, 1983

[51] Int. Cl.$^4$ .................. G01N 33/53; G01N 33/534; G01N 33/535

[52] U.S. Cl. ........................................ 435/7; 435/810; 436/500; 436/545; 436/804; 436/808

[58] Field of Search .................... 435/7, 810; 436/500, 436/545, 804, 808

[56] References Cited

U.S. PATENT DOCUMENTS 4,468,469  8/1984  Atkinson ..................... 436/808 X Primary Examiner—Sidney Marantz
Assistant Examiner—Cynthia Lee Foulke
Attorney, Agent, or Firm—Andrew L. Klawitter

[57] ABSTRACT

An improved immunoassay method, reagent means, test kit, and test device for determining an iodothyronine, e.g., thyroxine (T-4), in a biological fluid, usually serum or plasma, wherein 2-hydroxy-4-methoxybenzophenone-5-sulfonic acid (HMS), or a salt thereof, is employed as a blocking agent for the binding of iodothyronines to thyroxine binding protein (TBP). The present invention is particularly advantageous as applied to homogeneous competitive binding iodothyronine immunoassays employing labels which are participants in enzyme-catalyzed reactions. Such labels include enzyme substrates, coenzymes, enzyme inhibitors, enzyme prosthetic groups, and enzymes.

40 Claims, No Drawings

IODOTHYRONINE IMMUNOASSAYS EMPLOYING HMS AS TBP BLOCKING AGENT

BACKGROUND OF THE INVENTION

1. Field of the Invention

This invention relates to immunoassays for the determination of iodothyronines in biological fluids such as serum or plasma. In particular, the present invention relates to competitive binding immunoassay methods, reagent means, test kits, and test devices for determining iodothyronines in unextracted samples of serum or plasma through the use of blocking or dissociating agents for the binding of iodothyronines by thyroxine binding proteins (TBP) present in such samples.

The principal iodothyronines of clincal interest are 3,5,3',5'-tetraiodothyronine (thyroxine; T-4) 3,5,3'-triiodothyronine (T-3, or simply "triiodothyronine"); 3,3',5'-triiodothyronine ("reverse T-3"); and 3,3'-diiodothyronine. The quantitative determination of the concentration of the various iodothyronines, particularly the hormones T-4 and T-3, in the blood is of importance in the diagnosis of thyroid disorders.

In the blood, nearly all of the circulating iodothyronines are complexed with various carrier proteins including albumin, thyroxine binding prealbumin and thyroxine binding globulin (TBG), such carrier proteins being generically referred to herein as thyroxine binding protein (TBP). In order to measure the concentration of the total amount of an iodothyronine in a blood sample, such as serum or plasma, the TBP-bound forms must be dissociated to an analytically significant degree and the resulting total free iodothyronine determined. The dissociation of iodothyronines from TBP, particularly TBG, was originally accomplished by an extraction process (U.S. Pat. No. 3,414,383). Under the current state-of-the-art, iodothyronines can be determined by immunoassay in unextracted samples through the use of compounds found empirically to block, and cause dissociation of, TBP binding. In current competitive binding iodothyronine immunoassays, a test sample is combined with reagents including an antibody to the iodothyronine to be determined, a labeled form (e.g., radiolabeled) of such iodothyronine, and one or more TBP blocking agents. The iodothyronine in the sample complexed with TBP is dissociated therefrom and competes with labeled iodothyronine for binding to the antibody. The proportion of labeled iodothyronine that becomes antibody-bound compared to that which remains unbound from antibody is dependent on the total concentration of the iodothyronine in the sample and is measurable in a wide variety of ways depending on the particular immunoassay technique employed.

2. Description of the Prior Art

Various compounds have been discovered as useful TBP blocking agents, including tetrachlorothyronine [Mitsuma et al, *J. Clin. Endocrinol. Metab.* 33:365 (1971)], diphenylhydantoin [Lieblich and Utiger, *J. Clin. Invest.* 50:60a (1971)], salicylate [Larson, *Metab.* 20:976 (1971)], the various materials disclosed by Hollander (U.S. Pat. No. 3,928,553) and Chopra (U.S. Pat. No. 3,911,096), particularly 8-anilino-1-naphthalenesulfonic acid (ANS), and certain substituted phenylacetic acids, particularly fenclofenac and diclofenac (U.S. patent application Ser. No. 414,934, now U.S. Pat. No. 4,468,469 filed Sept. 3, 1982 and assigned to the present asignee). The structures and general properties of the known TBP blocking agents vary over an extremely wide range. The properties critical to operability as a TBP blocking agent in immunoassays, i.e., the ability to sufficiently dissociate iodothyronines from TBP at concentration levels insufficient to cause significant inhibition of the antibody binding reaction, are generally considered unpredictable from purely structural comparisons, although some theories of TBG blocking have been propounded [Brown and Metheany, *J. Pharm. Sci.* 63:1214 (1974)].

SUMMARY OF THE INVENTION

It has now been found that 2-hydroxy-4-methoxybenzophenone-5-sulfonic acid (HMS) and salts thereof are particularly advantageous TBP blocking agents for use in iodothyronine immunoassays. The blocking agent compound is included in the immunoassay reaction mixture at a concentration sufficient to release and block the binding of an analytically significant percentage of TBP-complexed iodothyronine, preferably more than 50% and usually more than 70%, while insufficient to interfere significantly with the binding of antibody with iodothyronine. While the precise concentrations of the blocking agent desired for a particular iodothyronine immunoassay will vary according to the iodothyronine under assay and the immunoassay technique followed, as well as other factors, the compound is normally used in concentrations in the reaction mixture of between about 0.1 millimolar (mM) and about 10 mM, preferably greater than about 0.25 mM, and usually less than about 5.0 mM. The HMS blocking agent of the present invention is added to the assay reaction mixture as the acid or an analytically acceptable salt form thereof, e.g., the sodium, potassium, lithium and ammonium salts.

HMS offers particular advantages as a TBP blocking agent in immunoassays. The compound has been found to be a particularly potent blocking agent. Dissociation of over 50% of TBP-bound iodothyronine in a few minutes is possible using reaction mixture concentrations as low as 1 mM, with concentrations of only 4 mM providing over 90% dissociation. HMS is highly water soluble and has been found to be effective over a fairly broad pH range, giving versatility to the design of test kits.

Additionally, HMS will exhibit no substantial inhibitory effect on the catalytic activity of many enzymes at concentrations in which it is an effective TBP blocking agent. By insubstantial inhibitory effect on enzymatic activity is meant that the rate of catalysis is not decreased more than about 70%, more usually less than 50%, and preferably less than 30%. Thus, this compound is further advantageous as a TBP blocking agent in homogeneous immunoassays wherein the label employed is a participant in an enzymatic reaction, e.g., an enzyme substrate, an enzyme inhibitor, a prosthetic group of an enzyme, a coenzyme, or an enzyme itself, or a fragment thereof. Prior art TBP blocking agents, particularly the most popular agent, ANS, can cause significant inhibition of enzyme reactions resulting again in decreased assay performance.

Therefore, HMS and its salts find novel use as TBP blocking agents in immunoassays in general, and are particularly advantageous when applied to homogeneous immunoassays, especially those in which the label employed is a participant in an enzyme-catalyzed reaction. The present invention also provides a reagent system for performing the novel immunoassays, particularly in the form of test kits and test devices commonly used in clinical laboratories.

DESCRIPTION OF THE PREFERRED EMBODIMENTS

HMS, having the formula:

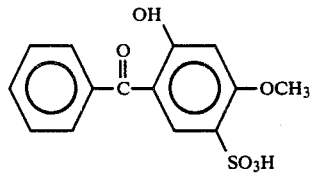

has been found to be particularly advantageous as a TBP blocking agent for use in iodothyronine immunoassays. It will, however, be evident to one of ordinary skill in the art that various modifications can be made to the basic benzophenone structure of the formula above without departing from the present inventive concept. Analogs possessing the advantageous TBP blocking agent features of the present invention will be considered as equivalents for the purposes of the claims hereof. For example, without limitation, the unsubstituted phenyl ring can be appropriately substituted such as with one or more substituents selected from alkyl, usually lower alkyl ($C_{1-4}$), e.g., methyl, ethyl, and propyl; alkoxy, usually lower alkoxy, e.g., methoxy and ethoxy; hydroxyl; halo; acid groups such as carboxylic and sulfonic acid groups and their alkyl homologs, and the like. Also, the substituents on the phenyl ring bearing the sulfuric acid group can be moved to other positions on the ring or removed, and the ring additionally substituted with appropriate groups as, for example, listed above.

The present invention has applicability to iodothyronine immunoassays in general. For the purposes hereof, an immunoassay will be understood to mean any assay based on antigen-antibody interactions and antibody will be understood to mean whole conventional or monoclonal antibody (e.g., of the IgG, IgM, IgA, etc., types) or an effective fragment thereof (e.g., Fab, F(ab'), etc. fragments of IgG). The most common type of immunoassay to which the present invention will be advantageously applied is the competitive binding immunoassay. In such an immunoassay for determining an iodothyronine, a test sample of body fluid, usually serum or plasma, is combined with an antibody to the iodothyronine under assay, a labeled form of the iodothyronine, and a blocking agent for TBP binding. The proportion of labeled iodothyronine that becomes bound to the antibody in competition with any iodothyronine in the sample compared to that which remains unbound is related to the concentration of the iodothyronine in the sample.

Both homogeneous and heterogeneous immunoassay techniques can be followed, the former being particularly preferred. In heterogeneous immunoassays, the antibody-bound form of the labeled iodothyronine is physically separated, as is known in the art, from the unbound form and the label measured in one or the other of the separated phases. Various different labels are known for use in heterogeneous immunoassays, including radioactive iosotopes (e.g., U.S. Pat. Nos. 4,111,656 and 3,911,096), fluorescers (e.g., U.S. Pat. Nos. 4,201,763; 4,171,311; 4,133,639; and 3,992,631), enzymes (e.g., U.S. Pat. No. 3,654,090), and so forth. In radioimmunoassays for iodothyronines it is particularly advantageous to use radioactive iodine as the label, substituting same for one of the native iodines in the iodothyronine.

In homogeneous immunoassays, which are particularly preferred in the present invention, the antibodybound form of the labeled iodothyronine expresses a different property from the unbound form and thus the separation step required in heterogeneous assays can be avoided. A wide variety of homogeneous immunoassay techniques are known in the art. Particularly preferred are those wherein the label which is chemically conjugated to the iodothyronine is an enzyme, or an enzyme fragment, e.g., a prosthetic group, or is a participant in an enzyme-catalyzed reaction, e.g., a substrate, a coenzyme, an inhibitor, an activator, or the like. The use of HMS may be somewhat restricted in immunoassays wherein a light emission, e.g., fluorescence or chemiluminescence, is the signal and is measured in the presence of the blocking agent. HMS has been found to absorb at wavelengths above 360 nanometers (nm) and, therefore, could potentially quench emissions in this region.

The present invention is particularly applicable to homogeneous competitive binding immunoassays wherein the label is a participant in an enzyme-catalyzed reaction. Such immunoassays include enzyme substrate-labeled techniques (see commonly assigned, copending U.S. patent application Ser. No. 894,836, filed Apr. 10, 1978—and corresponding U.K. patent specification No. 1,552,607); prosthetic group-labeled techniques [see U.S. Pat. No. 4,238,565 describing a particularly preferred system wherein the label is flavin adenine dinucleotide (FAD) and is measured by addition of apo(glucose oxidase)]; coenzyme-labeled techniques (see U.S. Ser. No. 894,836, supra; enzyme modulator-labeled techniques (see U.S. Pat. Nos. 4,134,792 and 4,273,866); and enzyme-labeled techniques (see U.S. Pat. Nos. 3,817,837 and 4,043,872). Other homogeneous competitive binding immunoassay techniques can be followed without departing from the present inventive concept. Further details are provided in commonly assigned, copending U.S. patent application Ser. No. 414,934, now U.S. Pat. No. 4,468,469 filed Sept. 3, 1982.

The biological fluid to be tested can be any in which the iodothyronine(s) of interest may be undesirably associated with binding proteins. In the usual situation, the biological fluid is a blood sample such as serum or plasma.

The reagent system of the present invention comprises all of the essential chemical elements required to conduct a desired iodothyronine immunoassay method encompassed by the present invention. The reagent means is presented in a commercially packaged form, as a composition or admixture where the compatibility of the reagents will allow, in a test device configuration, or as a test kit, i.e., a packaged combination of one or more containers holding the necessary reagents. Included in the reagent system are the reagents appropriate for the binding reaction system desired and having a compound of the present invention, e.g., HMS, as a TBP blocking agent. Such binding reaction reagents usually include, in addition to the present blocking agent, a labeled iodothyronine conjugate, antibody to the iodothyronine under assay, and possibly other TBP blocking agents as may be desired. Of course, the reagent system can include other materials as are known in the art and which may be desirable from a commercial and user standpoint, such as buffers, diluents, standards, and so forth. Particularly preferred is a test kit for the homogeneous competitive binding immunoassay of the present invention comprising (a) an antibody to the iodothyronine to be determined, (b) a labeled iodothyronine conjugate which has a detectable property which is altered when bound with the antibody and (c) a compound of the present invention as a TBP blocking agent. The specific label used will depend on the technique folowed, as described hereinabove. Also preferred is a test device comprising a reagent composition including an iodothyronine antibody, a labeled iodothyronine conjugate which has a detectable property which is altered when bound with the antibody, and a compound of the present invention as a TBP blocking agent, and a solid carrier member incorporated with the reagent composition. Some of the various forms of such test device are described in U.S. patent application Ser. No. 202,378, filed Oct. 30, 1980, now abandoned which is incorporated herein by reference, and which has been published as European patent application No. 51,213.

The present invention will now be illustrated, but is not intended to be limited, by the following examples.

EXAMPLES

I. Dissociation of Thyroxine from Human Serum Proteins by HMS

Radioactive iodine-labeled thyroxine ($^{125}$I-thyroxine obtained from New England Nuclear, Boston, MA USA) was equilibrated with 3.5 milliliter (mL) of normal human serum for 48 hours at 4° C. Aliquots of this serum [50 microliters ($\mu$L)] were added to 450 $\mu$L of 0.1 molar (M) sodium phosphate, pH 6.0, containing various concentrations of HMS to give the final concentrations given in Table 1. After 5 or 30 minutes of incubation at room temperature, a 500 $\mu$L aliquot was applied to a Sephadex column from a Seralute® thyroxine assay kit (Miles Laboratories, Inc., Ames Division, Elkhart, IN, USA), which has been equilibrated with 0.1 M sodium phosphate, pH 6.0. The total radioactivity applied to the columns was measured and the undissociated material was washed through the column. The columns were counted to determine the percentage of thyroxine dissociated from the serum proteins.

TABLE 1

| HMS Concentration Millimolar (mM) | Percent Dissociated in 5 Minutes | Percent Dissociated in 30 Minutes |
|---|---|---|
| 0 | 30 | 31 |
| 1 | 65 | 73 |
| 2 | 74 | 84 |
| 4 | 91 | 94 |
| 6 | 93 | 95 |

II. Effect of pH on the Dissociation of Iodothyronine From Serum Proteins by HMS Assays were performed in 3 ml polystyrene test tubes in duplicate. A solution (designated "MIX") was prepared containing 27 mL of 0.1 M sodium phosphate, at the stated pH, 73 mL of 21% polyethyleneglycol, 1.0 mM HMS, and 10 micrograms ($\mu$g) (40 $\mu$L) I-125-thyroxine for each 100 mL. Assay solutions are made up by addition of 50 $\mu$L of a serum sample, 0.1 mL of anti(thyroxine) antiserum diluted in 0.1 M sodium phosphate (at the given pH) and 1.0 mL of the MIX solution. Assays are included for maximum binding of label and nonspecific binding. The results were as follows:

TABLE 2

| pH | % Dissociated |
|---|---|
| 6.0 | 73 |
| 6.5 | 73 |
| 7.0 | 69 |
| 7.5 | 72 |

The data indicated that pH has essentially no effect on the efficiency of dissociation over the range 6.0–7.5.

III. Effect of HMS on the Activation of Apo(glucose oxidase) by an FAD-labeled Thyroxine Conjugate The activation of apoglucose oxidase was set up with different concentrations of HMS and performed at 37° C. Assays containing 50 mM sodium phosphate, pH 6.5, 200 mM glucose, 2.0 mM sodium dichlorohydroxybenzene sulfonate (DHSA), 25 $\mu$g/mL peroxidase, various concentrations of HMS and 2.5 nM final concentration of a FAD-thyroxine conjugate (see U.S. Pat. No. 4,213,893) were started by adding apo(glucose oxidase), 4-aminoantipyrine, and anti(glucose oxidase) at final concentrations of 125 nM, 400 $\mu$M, and 8 $\mu$L/mL respectively. The absorbance at 520 nm was recorded after a five minute incubation. The data are presented in Table 3 as a percentage of the absorbance recorded when no HMS is present.

TABLE 3

| HMS (mM) | % Activity |
|---|---|
| 0 | 100 |
| 0.05 | 100 |
| 0.10 | 100 |
| 0.50 | 99 |
| 1.00 | 97 |
| 5.00 | 86 |
| 10.00 | 72 |

IV. The Use of HMS in the Apoenzyme Reactivation Immunoassay System (ARIS) for Serum Thyroxine.

An ARIS procedure (see U.S. Pat. No. 4,238,565) was performed as follows. Standard curves for serum thyroxine were generated using an Ames/Gilford OPTIMATE™ instrument system (Miles Laboratories, Inc., Elkhart, IN, USA) with an automated sequential addition protocol. (Serum and antiserum were added to the reaction cup followed by an eighteen-minute preincubation. The FAD-conjugate and apoenzyme were added to initiate the assay. After a five-minute incubation at 37°, the absorbance at 520 nm was recorded.) The final concentrations of the reagents used in the assay are 50 mM sodium phosphate, pH 6.5, 2 mM dichlorohydroxybenzene sulfonate (DHSA), 25 $\mu$g/mL peroxidase, 200 mM glucose, 2 mM HMS, 50 $\mu$L/mL serum sample, 4 $\mu$L anti(thyroxine) antiserum, 10 $\mu$L anti(glucose oxidase) antiserum, 2.5 nM T-4-FAD conjugate, 50 nM apoglucose oxidase, and 320 nM 4-aminoantipyrine. The serum standards were prepared by spiking T-4, T-3 free human serum (AMF Biological and Diagnostic Products, Sequin, TX, USA) with thyroxine to give the desired total concentration. The results were as follows:

TABLE 4

| Thyroxine Standard (μg/L) | Absorbance |
|---|---|
| 0 | 0.239 |
| 20 | 0.278 |
| 40 | 0.315 |
| 80 | 0.406 |
| 120 | 0.529 |
| 200 | 0.821 |

With HMS as the iodothyronine dissociated agent, a correlation between the recorded absorbance at 520 nm and the concentrations of thyroxine in serum can be observed when using the homogeneous apoenzyme reactivation immunoassay system.

What is claimed is:

1. In an immunoassay method for determining an iodothyronine in a biological fluid,
 the improvement which comprises employing 2-hydroxy-4-methoxybenzophenone-5-sulfonic acid, or a salt thereof, as a blocking agent for the binding of said iodothyronine to thyroxine binding protein in said biological fluid.

2. The method of claim 1 wherein 2-hydroxy-4-methoxybenzophenone-5-sulfonic acid or a salt thereof is present in the assay reaction mixture at a concentration greater than about 0.1 mM.

3. The method of claim 1 wherein 2-hydroxy-4-methoxybenzophenone-5-sulfonic acid or a salt thereof is present in the assay reaction mixture at a concentration between about 0.25 mM and about 5.0 mM.

4. The method of claim 1 wherein said iodothyronine is thyroxine.

5. The method of claim 1 wherein said iodothyronine is triiodothyronine.

6. The method of claim 1 wherein said method is a competitive binding immunoassay method in which a sample of said biological fluid is combined with an antibody to said iodothyronine, a labeled form of said iodothyronine, and a blocking agent for the binding of said iodothyronine to thyroxine binding protein in said sample and wherein the proportion of labeled iodothyronine that becomes bound to said antibody compared to that which remains unbound is related to the concentration of said iodothyronine in said sample.

7. The method of claim 6 wherein the label in said labeled iodothyronine is radioactive iodine.

8. The method of claim 6 wherein said labeled iodothyronine comprises a conjugate of said iodothyronine chemically coupled with a participant in an enzyme-catalyzed reaction.

9. The method of claim 8 wherein said label is an enzyme substrate, a coenzyme, an enzyme inhibitor, a prosthetic group of an enzyme, or an enzyme.

10. The method of claim 1 wherein said biological fluid is serum or plasma.

11. A homogeneous immunoassay method for determining an iodothyronine in a biological fluid, comprising the steps of:
 (a) combining said biological fluid with a reagent system comprising (1) an antibody to said iodothyronine, (2) a labeled iodothyronine conjugate comprising a label which provides a detectable response which is measurably different when said conjugate is bound with said antibody compared to when not so bound, and (3) a thyroxine binding protein blocking agent comprising 2-hydroxy-4-methoxybenzophenone-5-sulfonic acid, or a salt thereof, and
 (b) measuring the detectable response of said label as a function of the amount of said iodothyronine in said fluid.

12. The method of claim 11 wherein 2-hydroxy-4-methoxybenzophenone-5-sulfonic acid, or a salt thereof is present in the assay reaction mixture at a concentration greater than about 0.1 mM.

13. The method of claim 11 wherein 2-hydroxy-4-methoxybenzophenone-5-sulfonic acid, or a salt thereof is present in the assay reaction mixture at a concentration between about 0.25 mM and about 5.0 mM.

14. The method of claim 11 wherein said iodothyronine is thyroxine.

15. The method of claim 11 wherein said iodothyronine is triiodothyronine.

16. The method of claim 11 wherein said label is a participant in an enzyme-catalyzed reaction.

17. The method of claim 16 wherein said label is an enzyme substrate, a coenzyme, an enzyme inhibitor, an enzyme prosthetic group, or an enzyme.

18. The method of claim 16 wherein said label is an enzyme prosthetic group which combines with an apoenzyme to produce an active enzyme whose activity is measured by its ability to catalyze a reaction producing a detectable product, the ability of said apoenzyme to combine with said prosthetic group in the labeled conjugate being altered by binding of said antibody with said labeled conjugate.

19. The method of claim 18 wherein said prosthetic group is flavin adenine dinucleotide and said apoenzyme is apo(glucose oxidase).

20. The method of claim 11 wherein said biological fluid is serum or plasma.

21. In a reagent system for the immunoassay determination of an iodothyronine in a biological fluid,
 the improvement which comprises 2-hydroxy-4-methoxybenzophenone-5-sulfonic acid, or a salt thereof, as a blocking agent for the binding of said iodothyronine to thyroxine binding protein in said biological fluid.

22. The reagent system of claim 21 wherein said iodothyronine is thyroxine.

23. The reagent system of claim 21 wherein said iodothyronine is triiodothyronine.

24. The reagent system of claim 21 further comprising an antibody to said iodothyronine and a labeled form of said iodothyronine.

25. The reagent system of claim 24 wherein the label in said labeled iodothyronine is radioactive iodine.

26. The reagent system of claim 24 wherein said labeled iodothyronine comprises a conjugate of said iodothyronine chemically coupled with a participant in an enzyme-catalyzed reaction.

27. The reagent system of claim 26 wherein said label is an enzyme substrate, a coenzyme, an enzyme inhibitor, a prosthetic group of an enzyme, or an enzyme.

28. A test kit for the homogeneous immunoassay determination of an iodothyronine in a biological fluid comprising:
 (1) an antibody to said iodothyronine,
 (2) a labeled iodothyronine conjugate comprising a label which provides a detectable response which is measurably different when said conjugate is bound with said antibody compared to when not so bound, and (3) a thyroxine binding protein blocking agent comprising 2-hydroxy-4-methoxybenzophenone-5-sulfonic acid, or a salt thereof.

29. The test kit of claim 28 wherein said iodothyronine is thyroxine.

30. The test kit of claim 28 wherein said iodothyronine is triiodothyronine.

31. The test kit of claim 28 wherein said label is a participant in an enzyme-catalyzed reaction.

32. The test kit of claim 31 wherein said label is an enzyme substrate, a coenzyme, an enzyme inhibitor, an enzyme prosthetic group, or an enzyme.

33. The test kit of claim 31 wherein said label is an enzyme prosthetic group which combines with an apoenzyme to produce an active enzyme whose activity is measured by its ability to catalyze a reaction producing a detectable product, the ability of said apoenzyme to combine with said prosthetic group in the labeled conjugate being altered by binding of said antibody with said labeled conjugate.

34. The test kit of claim 33 wherein said prosthetic group is flavin adenine dinucleotide and said apoenzyme is apo(glucose oxidase).

35. The test device for the immunoassay determination of an iodothyronine in a biological fluid, comprising the reagent system of claim 21 incorporated with a solid carrier member.

36. The test device of claim 35 wherein said reagent system comprises:
  (1) an antibody to said iodothyronine,
  (2) a labeled iodothyronine conjugate comprising a label which provides a detectable response which is measurably different when said conjugate is bound with said antibody compared to when not so bound, and
  (3) said blocking agent compound or salt thereof.

37. The test device of claim 36 wherein said label is a participant in an enzyme-catalyzed reaction.

38. The test device of claim 37 wherein said label is an enzyme substrate, a coenzyme, an enzyme inhibitor, an enzyme prosthetic group, or an enzyme.

39. The test device of claim 37 wherein said label is an enzyme prosthetic group which combines with an apoenzyme to produce an active enzyme whose activity is measured by its ability to catalyze a reaction producing a detectable product, the ability of said apoenzyme to combine with said prosthetic group in a labeled conjugate being altered by binding of said antibody with said labeled conjugate.

40. The test device of claim 39 wherein said prosthetic group is flavin adenine dinucleotide and said apoenzyme is apo(glucose oxidase).

* * * * *